(12) United States Patent
Bacon

(10) Patent No.: US 6,866,038 B2
(45) Date of Patent: Mar. 15, 2005

(54) FIRING FLAP DISPENSER

(75) Inventor: Raymond John Bacon, Hampshire (GB)

(73) Assignee: Clinical Designs Limited, Emsworth (GB)

( * ) Notice: Subject to any disclaimer, the term of this patent is extended or adjusted under 35 U.S.C. 154(b) by 0 days.

(21) Appl. No.: 10/470,229

(22) PCT Filed: Jan. 24, 2002

(86) PCT No.: PCT/GB02/00297

§ 371 (c)(1),
(2), (4) Date: Nov. 12, 2003

(87) PCT Pub. No.: WO02/058772

PCT Pub. Date: Aug. 1, 2002

(65) Prior Publication Data

US 2004/0065320 A1 Apr. 8, 2004

(30) Foreign Application Priority Data

Jan. 25, 2001 (GB) .............................. 0101944

(51) Int. Cl.$^7$ ............................................. A61M 11/00
(52) U.S. Cl. ............................ 128/200.23; 128/200.14; 128/203.15
(58) Field of Search ........................ 128/200.14, 200.23, 128/200.22, 203.12, 204.23, 203.15, 200.21; 251/4, 10

(56) References Cited

U.S. PATENT DOCUMENTS 2,002,835 A * 5/1935 Rose ........................... 251/10
2,716,013 A * 8/1955 Tinker .......................... 251/4
3,190,497 A * 6/1965 Anthon ........................ 222/64
3,456,646 A * 7/1969 Phillips et al. ......... 128/200.23
3,789,843 A * 2/1974 Armstrong et al. ..... 128/200.23
4,664,107 A * 5/1987 Wass ..................... 128/200.23
4,819,834 A * 4/1989 Thiel .......................... 222/355
4,972,830 A * 11/1990 Wong et al. ........... 128/200.21
5,031,610 A * 7/1991 Armstrong et al. ..... 128/200.23
5,069,204 A * 12/1991 Smith et al. ........... 128/200.23
5,119,806 A * 6/1992 Palson et al. .......... 128/200.14
2002/0056449 A1 * 5/2002 Wakefield et al. ..... 128/200.23

FOREIGN PATENT DOCUMENTS

| GB | 1012565 | * | 8/1965 | |
| GB | 1012565 | | 12/1965 | |
| GB | 2 263 873 | | 8/1993 | |
| GB | 2263873 A | * | 8/1993 | .......... A61M/15/00 |
| WO | WO 98/41254 | | 9/1998 | |

* cited by examiner

Primary Examiner—Henry Bennett
Assistant Examiner—Shumaya B. Ali
(74) Attorney, Agent, or Firm—Alfred A. Fressola; Ware, Fressola, Van Der Sluys & Adolphson LLP

(57) ABSTRACT

A breath actuated dispenser there-shown has a generally L-shaped hollow body 1 with a mouthpiece 2. An aerosol drug can 3 is mounted in the body. The can has a dispensing spout 4, which engages a receptor moulding 5 incorporating a living hinge 11, a movable outlet member 8 and a kink valve 9. A flap member 31 is pivotally mounted between the can and the receptor moulding. Breathing in through the dispenser by the patient will cause the flap to be drawn down against its spring 34. The outlet member is then tipped down by the spring 37 to point out of the mouthpiece 2, whence the dose is dispensed by opening of the kink valve.

19 Claims, 2 Drawing Sheets

FIRING FLAP DISPENSER

CROSS REFERENCE TO RELATED APPLICATIONS

This application is for entry into the U.S. national phase under §371 for International Application No. PCT/GB02/00297 having an international filing date of Jan. 24, 2002, and from which priority is claimed under all applicable sections of Title 35 of the United States Code including, but not limited to, Sections 120, 363 and 365(c), and which in turn claims priority under 35 USC §119 to Great Britain Patent Application No. 0101944.7 filed on Jan. 25, 2001.

TECHNICAL FIELD

The present invention relates to a dispenser, particularly though not exclusively for dispensing aerosol or powder borne medicaments.

BACKGROUND OF THE INVENTION

In my prior International Patent Application, PCT/GB98/00770, at least as amended on entry in the European Regional Phase, there is described and claimed:

A dispenser for a gaseous, gas borne or droplet substance, the dispenser including:
  a body having a mouthpiece with an inhalation/insufflation orifice at its end;
  a junction in the body for a source of gas or evaporable liquid comprising or containing the said substance (the source being carried by the body); and
  a breath actuable valve, for controlling the release of said gas or liquid, comprising:
    a valve inlet connected to the junction;
    a valve outlet;
    a flexible tube extending from the junction, between the inlet and the outlet, for receiving the said gas or liquid, the tube having a portion which is movable between a closed position in which the tube is kinked for closure of the valve and an open position in which the tube is un-kinked for opening of the valve; and
    a movable member, for moving the movable portion of the tube to control its kinking, and being movably mounted in the body for movement by the act of inhalation from a rest position towards the orifice—or at least in the direction of air flow through the dispenser;
  the tube being kinked to an obturating extent when the movable member is in a rest position and un-kinked when the movable member is moved on inhalation for release of the gas or liquid.

Such a dispenser can loosely be classed as a breath actuated, kink valve dispenser and is referred to herein as "My Earlier Breath Actuated, Kink Valve Dispenser".

The main embodiments of My Earlier Breath Actuated, Kink Valve Dispenser included a piston acted on by a differential breath induced pressure. The resultant force generated is generally sufficient to operate the dispenser by drawing the piston towards the dispenser's mouthpiece and extending and opening the kink valve. Nevertheless, I feel that the dispenser is susceptible of some improvement.

SUMMARY OF THE INVENTION

The object of the present invention is to provide improved breath actuated, kink valve dispensers, in particular having spring assistance to open the kink valve.

According to the invention I provide a dispenser for a gaseous, gas borne or droplet substance contained in a source thereof, the dispenser including in common with My Earlier Breath Actuated, Kink Valve Dispenser:
  a body with a mouthpiece;
  a junction in the body for the substance source; and
  a breath actuable valve, for controlling the release of the gas or liquid containing or comprising the substance, the valve comprising:
    a flexible tube for receiving the said gas or liquid, the tube extending from a valve inlet connected to the junction and having a portion which is kinkable for closure of the valve and movable to an open position in which the tube is un-kinked for opening of the valve; and
    an outlet member arranged for movement in the body on inhalation to un-kink the valve;
  the tube being kinked to an obturating extent when the outlet movable member is in a ready position and un-kinked when the outlet movable member is moved on inhalation for release of the gas or liquid;
the dispenser also including:
  a sear to hold the outlet movable member in the ready position closing of the tube by kinking prior to inhalation and
  a breath actuatable flap arranged in the body for movement on inhalation to release the sear and allow the outlet movable member to move for release of the gas or liquid.

Preferably, the junction is movably arranged in the body for limited movement with the source on depression thereof for release of the substance, the body preferably having grooves in which protrusions on the junction engage.

Normally the dispenser will include a spring acting between the junction and the body for resisting source-depression movement of the junction.

Preferably, the junction is a receptor integrally moulded with the flexible tube and the outlet member, the moulding including a living hinge connecting the receptor and the outlet member. The moulding can have resilient bias of the outlet member towards an un-kinked condition of the flexible tube.

In accordance with a particular feature of the invention, the dispenser includes a spring for biasing the outlet member towards the un-kinked condition of the flexible tube. The spring can be integrally moulded with the body.

The body can include at least one abutment member for pivoting the outlet member on source depression movement of the receptor.

In the preferred embodiment, the outlet member has an opening or openings through which a finger on the abutment member(s) can pass after pivotal movement of the outlet member caused by abutment of the abutment members with the outlet member, the arrangement being such that the finger(s) engage on an opposite side of the outlet member on return movement of the receptor.

The breath actuatable flap can be pivotably mounted in the body. It can include a resilient member biasing the flap to a movable-member-engaging position, the flap being arranged to engage a formation in the body.

Preferably:
  the outlet member has a respective nib for engaging the sears on the flap;
  the flap is U shaped to allow an outlet stem of the source to pass the flap;
  the springs are in a relaxed state when the source is not depressed to dispensing of a dose.

BRIEF DESCRIPTION OF THE DRAWINGS

To help understanding of the invention, a specific embodiment thereof will now be described by way of example and with reference to the accompanying drawings, in which.

DETAILED DESCRIPTION

Figure 1:
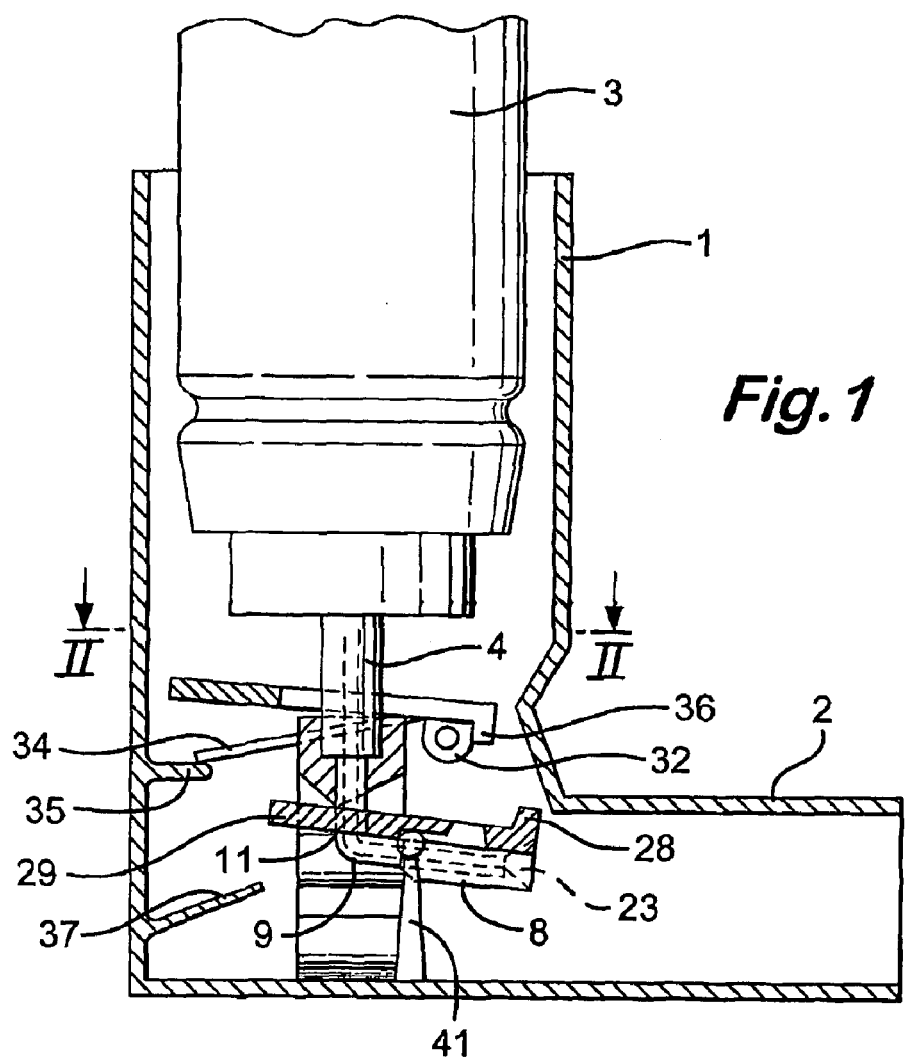
FIG. 1 is a cross-sectional side view of a dispenser of the invention.
Figure 2:
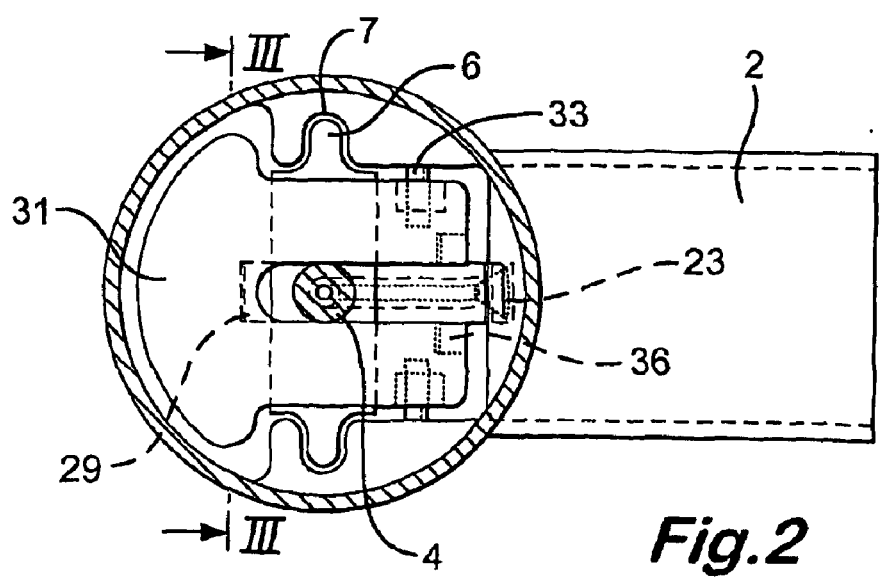
FIG. 2 is a cross-sectional plan view on the line II—II in FIG. 1.
Figure 3:
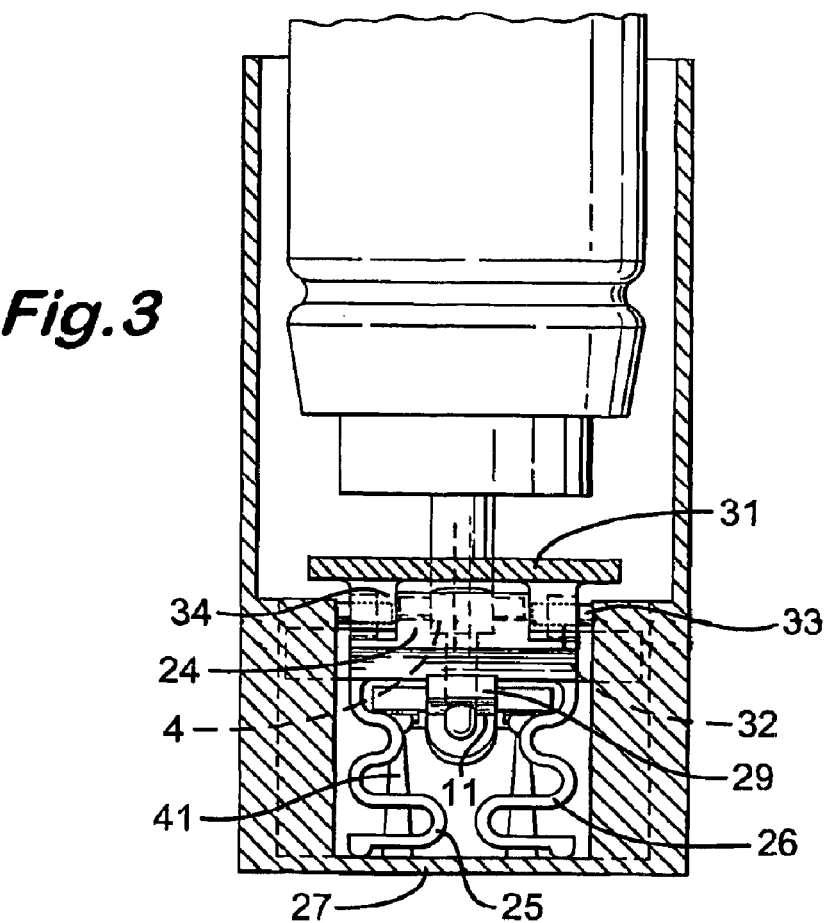
FIG. 3 is a cross-sectional end view on the line III—III in FIG. 2.
Figure 4:
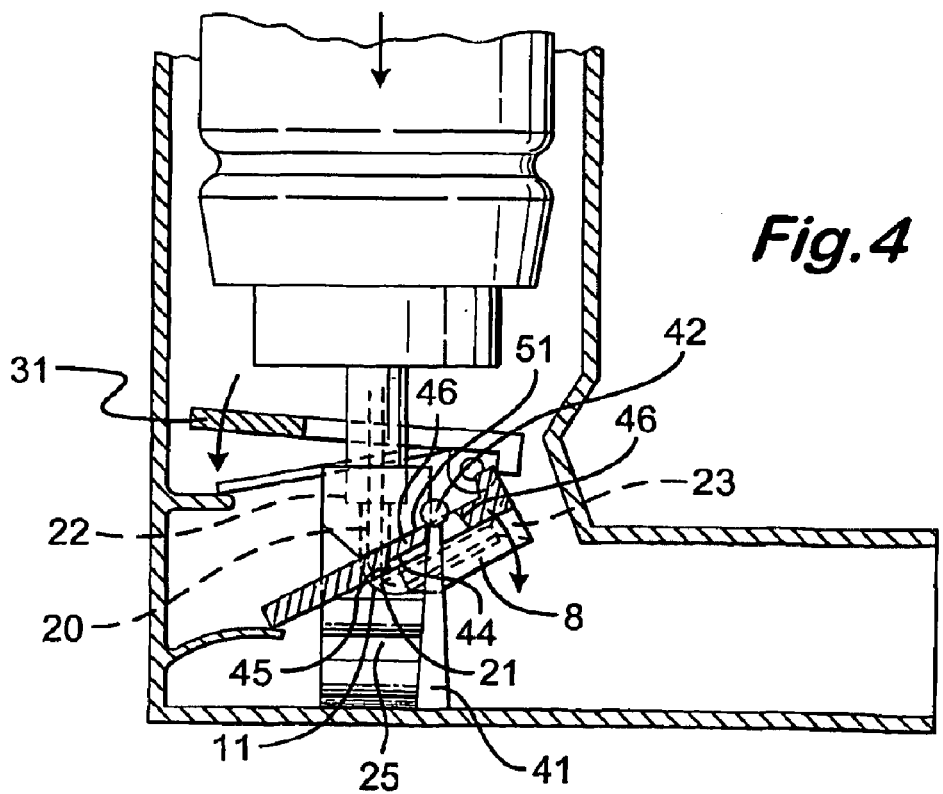
FIG. 4 is a view similar to FIG. 1 of the dispenser primed and cocked ready for use.

Referring to the drawings, the breath actuated dispenser there-shown has a generally L-shaped hollow body 1 with a mouthpiece 2. An aerosol drug can 3 is mounted in the body with good clearance to allow breathing through the body when the can is installed. The can has a dispensing spout 4, which engages a receptor moulding 5, the receptor moulding being engaged in the body via lugs 6 in slots 7 and incorporating a movable outlet member 8 and a kink valve 9. The parts (other than the can) are of injection moulded plastics material.

The outlet member 8 is connected to the main receptor moulding part by a living hinge 11. The receptor is moulded with the outlet member angled down with respect to the use orientation and a linear passage 20 through it. The central portion 21 of the passage has a thin wall thickness, whereby when the flap is hinged up, the passage kinks and closes. The upper end 22 of the passage is of larger diameter to receive the spout of the can. The lower end of the passage forms a spray nozzle 23, which is directed in accordance with the angle of the outlet member.

The receptor has a main spring moulding 24 fitted to it. This moulding has two depending springs 25,26, which are serpentine and of a length to abut a bottom 27 of the body and normally urge the receptor into its upper position.

A generally U-shaped flap member 31 is mounted between the can and the receptor moulding, the dispensing spout 4 being in the centre of the U, whose ends have apertured depending lugs 32. The lugs engage pips 33 in the wall of the body. A resilient under-flap 34, moulded integrally with the flap 31, abuts a protrusion 35 on the wall of the body opposite from the mouthpiece, whereby the flap 31 is angled slightly upwards when the can is upright. Beyond the lugs 33 the U has a pair of lips 36 on the arms of the U at their ends. These depend as a paired sear. The arrangement of the flap is such that breathing in through the dispenser causes the flap to deflect downwards against the light force of the resilient flap 34, with air escaping around the edge of the flap.

At its spray nozzle the outlet member has a pair of nibs 28 which can engage with the sear pair 36. The opposite end of the outlet member—beyond the living hinge 11 and eccentric from its central axis—has a finger 29, which abuts a spring 37 extending from the body below the protrusion 35. The arrangement is such that when the sear engages the movable member, the spring is loaded and urges the nozzle 23 downwards.

Extending up from the bottom of the body—inwards of the mouthpiece—is a generally Y-shaped resilient tongue 41 having two fingers 42 extending towards each other. The tongue extends transversely of the body—with substantial clearance so as not to inhibit air flow—whereby it is resilient at its ends for movement of the fingers towards or away from the mouthpiece. The outlet member has lips 43 running along it. They each have a rebate 44 on their undersides, arranged to be engaged by the fingers 42, which are urged to their stop ends 45 when the outlet member is angled downwards. The other ends 46 of the rebates are open to the top surface of the lips, so that the fingers can pass through.

The action of the dispenser is as follows:

In use, the patient depresses the can 3 in the body 4. This action presses the dispensing spout 4 towards the receptor moulding 5. The latter is moved forwards against the main reaction spring 25,26. When the compression in this reaches its design level, a dose is released into the tube 21 of the kink valve, which is kinked and holds the dose.

The depression has moved the living hinge 11 down and with it the pivoted outlet member 8. This is pivoted upwards about the hinge by action of the upstanding tongue 41 and in particular its end fingers 42. The fingers travel up the rebate 44 and through the open ends 46. At the same time, the back end 29 of the outlet member engages its spring 37 for urging it up and the nozzle down. The angle of the member is determined by a bevel 51 on the bottom of the receptor moulding and the member is controlled to be such that the nibs 28 on the end upper nozzle end engage with the corresponding the sear pair 36.

Prior to the depression of the can, the flap 31 is held up by its spring 34. On depression the flap is itself slightly depressed by the valve body 1 of the can, so that the sear is in position to be engaged by the lip. Final depression of the can causes the fingers 42 to pass out of the open ends 46 to disengage above the outlet member. The dispenser is now primed with a dose retained by the kink valve and its mechanism cocked.

Breathing in through the dispenser by the patient will cause the flap to be drawn down against its spring 34. The sear is lifted and releases the nibs. The outlet member is then tipped down by the spring 37 to point out of the mouthpiece 2, whence the dose is dispensed by opening of the kink valve.

Release of the can allows the main spring to lift the receptor moulding. At this stage, the fingers 42 are above the outlet member. The former bears on the top surface of the latter, keeping it angled down. However, the fingers come into registration with the openings 46 and are drawn through the openings 46, with flexure of the tongue 41. The mechanism is ready for another cocking and dispensing action. It should be noted that in this ready state, the springs 25,26, 34,37 are all in their relaxed state, so that the device is not stored with them under load, which would tend to cause them to relax, being of plastics material.

What is claimed is:

1. A dispenser for a gaseous, gas borne or droplet substance contained in a source thereof, the dispenser including:

a body with a mouthpiece;

a junction in the body for the substance source; and a breath actuable valve, for controlling the release of the gas or liquid containing or comprising the substance, the valve comprising:

a flexible tube for receiving the said gas or liquid, the tube extending from a valve inlet connected to the junction and having a portion which is kinkable for closure of the valve and movable to an open position in which the tube is un-kinked for opening of the valve; and an outlet member arranged for movement in the body on inhalation to un-kink the valve;

the tube being kinked to an obturating extent when the outlet movable member is in a ready position and un-kinked when the outlet movable member is moved on inhalation for release of the gas or liquid;

the dispenser also including:

a sear to hold the outlet movable member in the ready position closing of the tube by kinking prior to inhalation and a breath actuatable flap arranged in the body for movement on inhalation to release the sear and allow the outlet movable member to move for release of the gas or liquid.

2. A dispenser as claimed in claim 1, wherein the junction is movably arranged in the body for limited movement with the source on depression thereof for release of the substance, the body preferably having grooves in which protrusions on the junction engage.

3. A dispenser as claimed in claim 2, including a spring acting between the junction and the body for resisting source-depression movement of the junction.

4. A dispenser as claimed in claim 3, wherein the junction is a receptor integrally moulded with the flexible tube and the outlet member, the moulding including a living hinge connecting the receptor and the outlet member.

5. A dispenser as claimed in claim 4, wherein the moulding has resilient bias of the outlet member towards an un-kinked condition of the flexible tube.

6. A dispenser as claimed in claim 5, including a spring for biasing the outlet member towards the un-kinked condition of the flexible tube.

7. A dispenser as claimed in claim 6, wherein the spring is integrally moulded with the body.

8. A dispenser as claimed in claim 4, wherein the body includes at least one abutment member for pivoting the outlet member on source depression movement of the receptor.

9. A dispenser as claimed in claim 8, wherein the outlet member has an opening or openings through which a finger on the abutment member(s) can pass after pivotal movement of the outlet member caused by abutment of the abutment members with the outlet member, the arrangement being such that the finger(s) engage on an opposite side of the outlet member on return movement of the receptor.

10. A dispenser as claimed in claim 9, wherein the breath actuatable flap is pivotably mounted in the body.

11. A dispenser as claimed in claim 8, wherein the breath actuatable flap includes a resilient member biasing the flap to a movable-member-engaging position, the flap being arranged to engage a formation in the body.

12. A dispenser as claimed in claim 11, wherein the outlet member has a respective nib for engaging the sears on the flap.

13. A dispenser as claimed in claim 12, wherein the flap is U shaped to allow an outlet stem of the source to pass the flap.

14. A dispenser as claimed in claim 13, wherein its springs are in a relaxed state when the source is not depressed to dispensing of a dose.

15. A dispenser as claimed in claim 1, wherein the junction is a receptor integrally moulded with the flexible tube and the outlet member, the moulding including a living hinge connecting the receptor and the outlet member.

16. A dispenser as claimed in claim 1, wherein the moulding has resilient bias of the outlet member towards an un-kinked condition of the flexible tube.

17. A dispenser as claimed in claim 1, wherein the breath actuatable flap is pivotably mounted in the body.

18. A dispenser as claimed in claim 1, wherein the outlet member has a respective nib for engaging the sears on the flap.

19. A dispenser as claimed in claim 1, wherein its springs are in a relaxed state when the source is not depressed to dispensing of a dose.

* * * * *